US008435200B2

(12) United States Patent
Yoshikawa

(10) Patent No.: US 8,435,200 B2
(45) Date of Patent: May 7, 2013

(54) INGROWN NAIL CORRECTING DEVICE

(76) Inventor: Masanori Yoshikawa, Kumamoto-ken (JP)

(*) Notice: Subject to any disclaimer, the term of this patent is extended or adjusted under 35 U.S.C. 154(b) by 472 days.

(21) Appl. No.: 12/614,002

(22) Filed: Nov. 6, 2009

(65) Prior Publication Data
US 2010/0160845 A1    Jun. 24, 2010

(30) Foreign Application Priority Data

Dec. 22, 2008  (JP) ................ 2008-326137
Feb. 12, 2009  (JP) ................ 2009-029812
Jul. 24, 2009  (JP) ................ 2009-173528

(51) Int. Cl.
*A61F 5/00*  (2006.01)
(52) U.S. Cl.
USPC .......................................... 602/31
(58) Field of Classification Search ........ 602/22, 602/30, 31; 132/73, 76.2
See application file for complete search history.

(56) References Cited

U.S. PATENT DOCUMENTS

| | | | | |
|---|---|---|---|---|
| 884,376 A * | 4/1908 | Foster | | 602/31 |
| 1,451,311 A * | 4/1923 | Smith | | 602/31 |
| 1,708,716 A * | 4/1929 | Andersen | | 602/31 |
| 1,772,130 A * | 8/1930 | Crenshaw | | 602/31 |
| 1,785,376 A * | 12/1930 | Buckner | | 602/31 |
| 2,024,412 A * | 12/1935 | Wilson | | 602/31 |
| 2,202,926 A * | 6/1940 | Schmidthofer | | 602/31 |
| 2,920,621 A * | 1/1960 | Fettig | | 602/31 |
| 3,173,416 A * | 3/1965 | Rederich | | 602/31 |
| 3,799,160 A * | 3/1974 | Hahn | | 602/31 |
| 5,613,503 A * | 3/1997 | Penner | | 128/892 |
| 6,050,966 A * | 4/2000 | Wilberscheid | | 602/31 |
| 7,008,391 B2 * | 3/2006 | Machida | | 602/30 |
| 8,137,297 B2 * | 3/2012 | Ishida et al. | | 602/30 |
| 2009/0048551 A1 * | 2/2009 | Liberson | | 602/31 |

FOREIGN PATENT DOCUMENTS

| JP | 8-215227 | 8/1996 |
|---|---|---|
| JP | 3091516 | 2/2003 |
| JP | 2003-265508 | 9/2003 |

* cited by examiner

*Primary Examiner* — Patricia Bianco
*Assistant Examiner* — Raymond E Harris
(74) *Attorney, Agent, or Firm* — Jordan and Hamburg LLP

(57) ABSTRACT

The ingrown nail correcting device made of a resilient hard synthetic resin comprises an ingrown nail correcting device main body, an engaging member part curved into a hook shape to engage the ingrown nail and arranged at the front end of the ingrown nail correcting device main body, and a lever member inclined obliquely upward at an angle of 5 to 25 degrees with respect to the ingrown nail correcting device main body, and continuously arranged at a base end of the ingrown nail correcting device main body. The part between the ingrown nail correcting device main body and the lever member which are continuously arranged, is formed to serve as a fulcrum part.

7 Claims, 12 Drawing Sheets

INGROWN NAIL CORRECTING DEVICE

BACKGROUND OF THE INVENTION

1. Field of the Invention

This invention relates to an ingrown nail correcting device for correcting an ingrown nail by being fitted to a toe or a finger, or particularly to a big toe or a thumb having an ingrown nail.

2. Description of the Prior Art

Ingrown nail correcting devices of various shapes and structures have been developed so far. Such conventional ingrown nail correcting devices include, for example, an ingrown nail correcting device comprising an elastic correcting member having rubber elasticity or a resilient metal plate which is provided with hook-shaped engaging members on both longitudinal side-ends thereof to hook both side-ends of the ingrown nail, as described in the Patent Document 1, an ingrown nail correcting device made of a shape-memory alloy or a shape-memory resin which is bonded onto a dorsum of the nail and heated to bend the ingrown nail in the correcting direction, as described in the Patent Document 2, and an ingrown nail correcting device, comprising a long and narrow resilient thin plate having an engaging member part formed by folding back a front end downward so as to hook the front end part of the ingrown nail, which is fixed to the upper face of the nail by adhesive tape to maintain the state that the engaging member part is engaged with the front end part of the ingrown nail, as described in the Patent Document 3.

Such conventional ingrown nail correcting devices include:

[Patent Document 1] Patent Publication No. 2003-265508,
[Patent Document 2] Patent Publication No. H8-215227, and
[Patent Document 3] Utility Model Registration No. 3091516.

However, in the ingrown nail correcting device having the structure as described in the Patent Document 1, the elastic correcting member having the rubber elasticity is structured so that it may apply the elastic contraction force in the direction of the width of the nail. Therefore, the elastic contraction force largely acts on the engaging members on both sides of the elastic correcting member engaged with both side-ends of the ingrown nail, as the action force works in the direction of narrowing the width between the two side-ends of the ingrown nail, while the action force working in the direction of pulling the ingrown nail up, or in other words in the direction of correcting the ingrown nail is small. Therefore, the force does not work effectively to correct the ingrown nail, which represents a problem.

According to the ingrown nail correcting device made of the shape-memory alloy or the shape-memory resin as described in the Patent Document 2, when the adhesive force of the adhesive agent for bonding the correcting device to the dorsum of the nail is weak, the correcting device is easily removed from the dorsum of the nail and the correction cannot be performed. On the other hand, when the adhesive force is strong, removal of the correcting device from the nail becomes difficult, which is also a problem. In addition, since the correcting device needs to be heated by a dryer or warm water to correct the ingrown nail, it is difficult to exert the corrective force continuously for a long time, and the correction cannot be performed as well when heating is stopped as the correcting device returns into the original shape, which also represents a problem.

According to the ingrown nail correcting device as described in the Patent Document 3, the correcting device comprises the long and narrow resilient thin plate having the engaging member part formed by folding back the front end downward so as to hook the front end part of the ingrown nail. Therefore, there is an advantage that the engaging member part can easily hook the front end part of a side-end edge or a side-end edge on the other side of the ingrown nail and can be easily fitted to the ingrown nail when using the correcting device. However, even when the correcting device is fixed onto the upper face of the nail by the adhesive tape in the state that the engaging member part may hook the front end part of the ingrown nail, the engaging member part hardly has a sufficient corrective force for pulling the ingrown nail up. In addition, even when the correcting part of the device is resiliently deformed toward the upper face of the ingrown nail positively with the front end of the ingrown nail serving as a fulcrum so that the engaging member part may have the corrective force for pulling the ingrown nail up by the resilience, the corrective force is applied in the direction of moving the engaging member part forward from and off the front end of the ingrown nail but is hardly applied in the direction for correcting the ingrown nail since the fulcrum exists at the front end of the ingrown nail. Thus, an effective corrective force cannot be obtained, which represents a problem.

SUMMARY OF THE INVENTION

This invention is developed in view of the above-mentioned problems. The purpose of this invention is to provide an ingrown nail correcting device which not only facilitates fitting of the correcting device to the ingrown nail but also corrects the ingrown nail while exerting the effective and stable corrective force on the ingrown nail over a long period of time by applying leverage.

To achieve the above-mentioned purpose, the ingrown nail correcting device of this invention formed of a hard resilient plate member, as described in a first aspect, comprising an ingrown nail correcting device main body, a hook-shaped engaging member part formed at the front end thereof to hook the ingrown nail, and a lever member formed in an integrating manner at a base end of the main body to incline obliquely upward with respect to the main body at an angle of 5 to 25 degrees, in which a bent part between the continuously-arranged main body and the lever member serves as a fulcrum part and the lever member is fixed onto the nail by a fixing tape like an adhesive tape.

In the invention described in a second aspect, the ingrown nail correcting device, which is structured as mentioned above is formed so that the lateral width between two side-end faces may be narrowed gradually from the longitudinal middle part to the front end. Further, at least one of the side-end faces of the main body, which is positioned on the affected side of the ingrown nail, is formed to be a curved side-end face having a projecting arc shape so that the side part may serve as an affected area protecting element.

Further, in the invention described in a third aspect, the main body is curved to have a gently projecting arc shape from the fulcrum part toward the front end part.

Furthermore, in the invention described in a fourth aspect, a vent hole is formed in the lever member in a manner of penetrating through the upper and lower faces. The main body may be formed of a thin metal plate, and, it is preferable to form it with a robustly resilient hard synthetic resin like a polycarbonate resin, in particular, as described in another aspect.

BRIEF DESCRIPTION OF THE DRAWINGS

The drawings show embodiments of this invention in which.

PREFERRED EMBODIMENTS OF THE INVENTION

Figure 1:
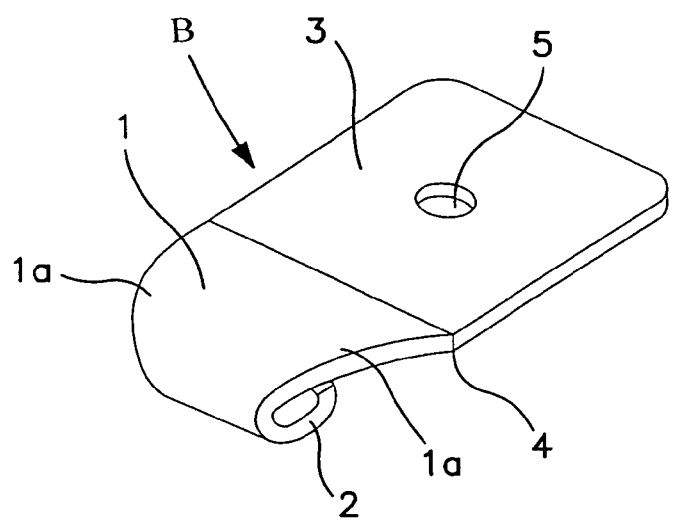
FIG. 1 is a perspective view of the ingrown nail correcting device according to the first embodiment of this invention.
Figure 2:
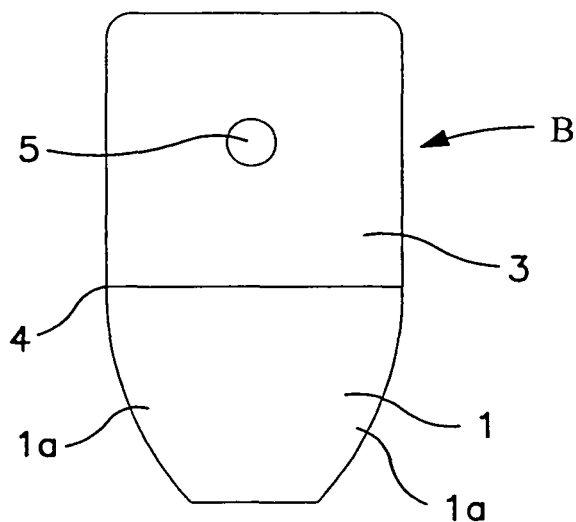
FIG. 2 is a plan view of the ingrown nail correcting device.

The first embodiment of the present invention is explained hereinafter based on the drawings. As shown in FIGS. 1 and 2, the ingrown nail correcting device B comprises the ingrown nail correcting device main body 1, of which the length in front and back direction is formed to be a little longer than the length from the front end to the base end of the nail A and the lateral width of a base end part thereof is formed to be ½ to ⅓ of lateral width of the nail A, an engaging member part 2 which is formed at the front end of the main body 1 in a manner of being folded backward and extending under the main body 1 to form a hook-like shape, and a lever member 3 which has a flat rectangular plate-like shape and gently inclines obliquely upward from the base end part of the main body 1 in the rear direction. A joint part of the base end of the main body 1 and the front end of the lever member 3 is formed to be a fulcrum part 4. Further, a lower face of the engaging member part 2 and a lower face of the lever member 3 are arranged on the substantially same horizontal plane.

With regard to the material of the ingrown nail correcting device B, it may be formed with a thin metal plate, however, it is preferable to use a synthetic resin like a polycarbonate resin or a hard vinyl chloride resin having robust resilience, or in particular to use a polycarbonate resin. The specific size of the ingrown nail correcting device B is as follows. Namely, the thickness is about 1 mm, the length from the front end of the main body 1 to the rear end (the base end) of the lever member 3 is about 18 mm, the width of base end part of the main body 1 and the width of the lever member 3 is 10-12 mm each, the length of the main body 1 is 8 mm, the lateral width of the front end of the main body 1 is 5 mm, the length of the engaging member part 2 is about 4 mm, the width of the front end part of thereof is about 5 mm, and the clearance between the lower face of the front end part of the main body 1 and the front end of the engaging member part 2 is 1 mm, however, the size is not particularly limited to these dimensions.

The bending angle at the fulcrum part 4 formed at the part between the main body 1 and the lever member 3 which are continuously arranged, or in other words, the angle θ formed by the horizontal plane extending backward from the base end of the main body 1 and the lever member 3 is formed to be 5 to 25 degrees, or more preferably, a gentle angle of inclination of 10 to 15 degrees. In other words, the angle formed by the upper surface of the main body 1 and the upper face of the lever member 3 is formed to be 155 to 175 degrees, or more preferably 165 to 170 degrees.

Further, the lateral width between the two side ends of the main body 1 is formed to become gradually smaller from the base end toward the front end. The narrower part protruding forward from the front end is bent in a manner of being folded down and then backward to form the engaging member part 2, as mentioned above. Both of the side-end faces of the part from the base part to the front end of the main body 1 are respectively curved to have a gentle outward projecting arc shape instead of linearly narrowing the lateral width of the part, and the two side parts of the narrowing part are formed to project outward to the extent possible. The curved side parts having the projecting arc shape are formed to be affected area protecting parts 1a, 1a. The area from the base part to the front end part of the main body 1 is made to curve upward to form a gently projecting arc shape seen from the side.

The vent hole 5 penetrating through the upper and lower surfaces is formed in the center part or in the rear part of the lever member 3 which covers the root area of the nail or the nail matrix, so that the vent hole 5 can prevent the nail matrix from becoming stuffy when the ingrown nail correcting device B is fitted onto the nail. The shape of the vent hole 5 may be a circle, a cross, or may be other shapes.

Figure 3:
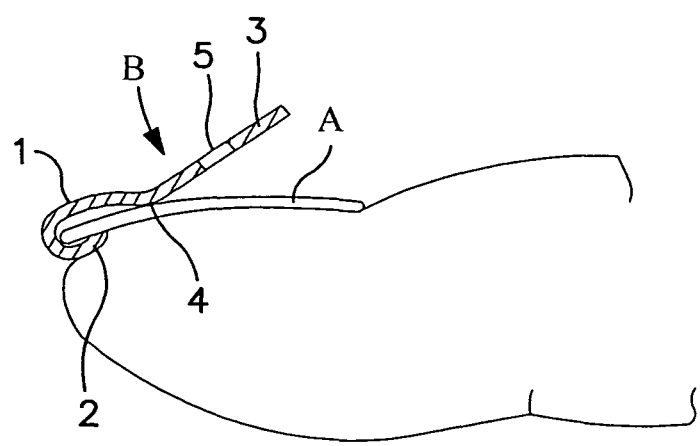
FIG. 3 is a longitudinal side elevation view of the ingrown nail correcting device in the state that the engaging member part is engaged with the front end of the nail.
Figure 4:
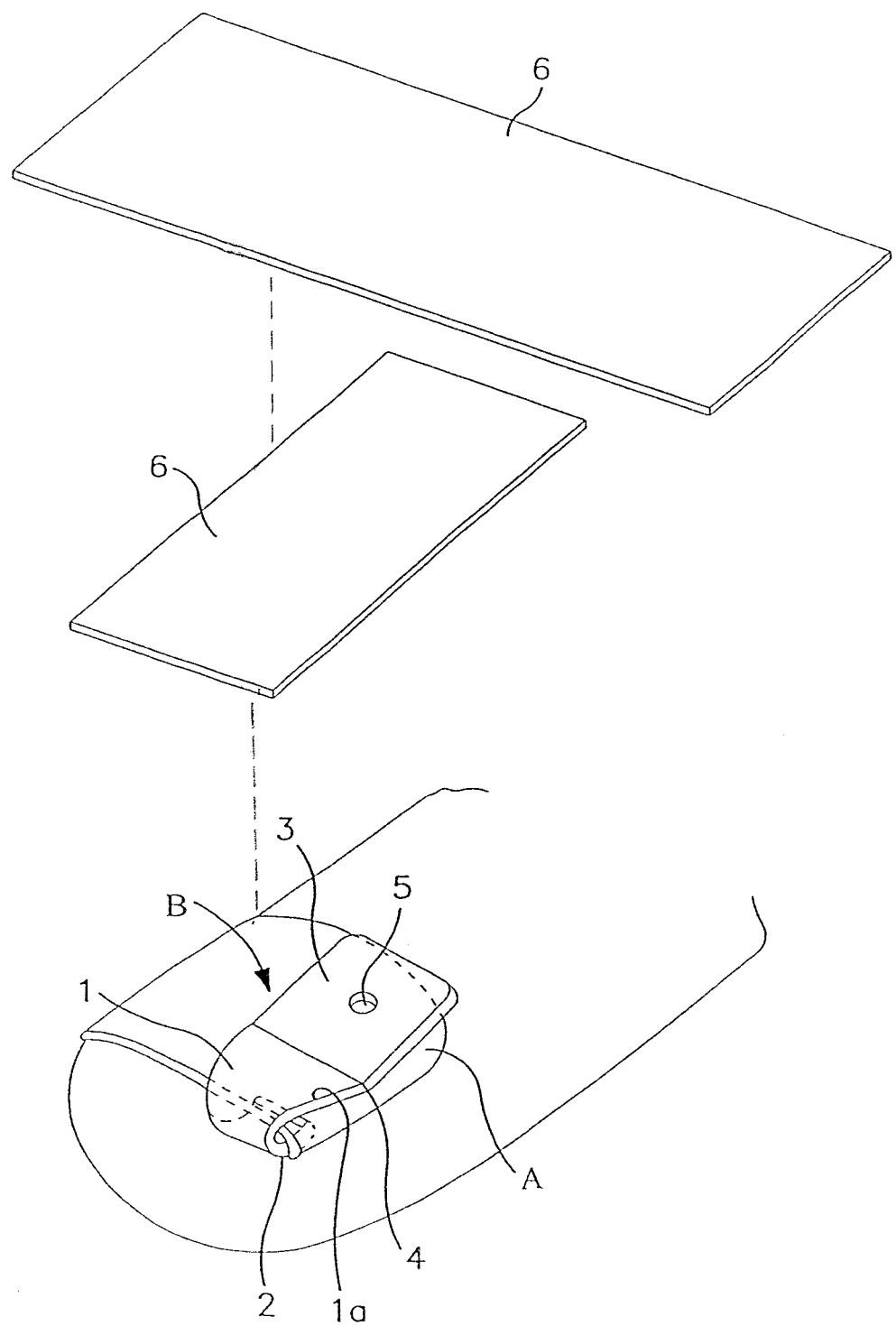
FIG. 4 is an exploded perspective view of the state that the ingrown nail correcting device is fixed by the adhesive tape.

The ingrown nail is corrected using the ingrown nail correcting device B, which is structured as mentioned above, in a manner as described below. Namely, when the nail of a first toe or a thumb has the ingrown nail on one side, for example, the ingrown nail correcting device B is placed on the side of the ingrown nail part, and the engaging member part 2 hooks the front end of the ingrown nail in an engaging manner as shown in FIGS. 3 and 4 so that the fulcrum part 4 may be received by the upper face of the nail A, and that the upper part of the front end of the side end of the nail A which is ingrown may be covered by the affected area protecting part 1a which projects outward on the side of the main body 1 to have the projecting arc shape.

After that, the lever member 3 inclining obliquely upward to the rear side from the base end of the main body 1 via the fulcrum part 4 is pressed down against the dorsum of the toe or the thumb until no inclination is shown, while allowing resilient deformation, and the main body 1 is moved in the erecting direction by the leverage having the pressing force of the lever member 3 as the force point and the fulcrum part 4 as the fulcrum, so that the action force works in a manner that the engaging member part 2 engaged with the front end of the ingrown nail is pulled up and the ingrown nail is resiliently corrected.

In this occasion, if the angle of inclination of the lever member 3 with respect to the main body 1 is set to be 5 degrees or less, the lever member 3 immediately comes into contact with the nail A when the lever member 3 is pressed down, and a sufficient corrective force by the leverage is not exerted by the engaging member part 2 engaged with the ingrown nail. If the angle of inclination is set to be 25 degrees or above, large resilient resistance is generated to press the lever member 3 down to the upper surface of the nail, and the corrective force for lifting the ingrown nail up by the engaging member part 2 becomes too large. Therefore, the angle of inclination of the lever member 3 inclining obliquely upward with respect to the main body 1 is set to be 5 to 25 degrees or preferably be 10 to 15 degrees.

Figure 5:
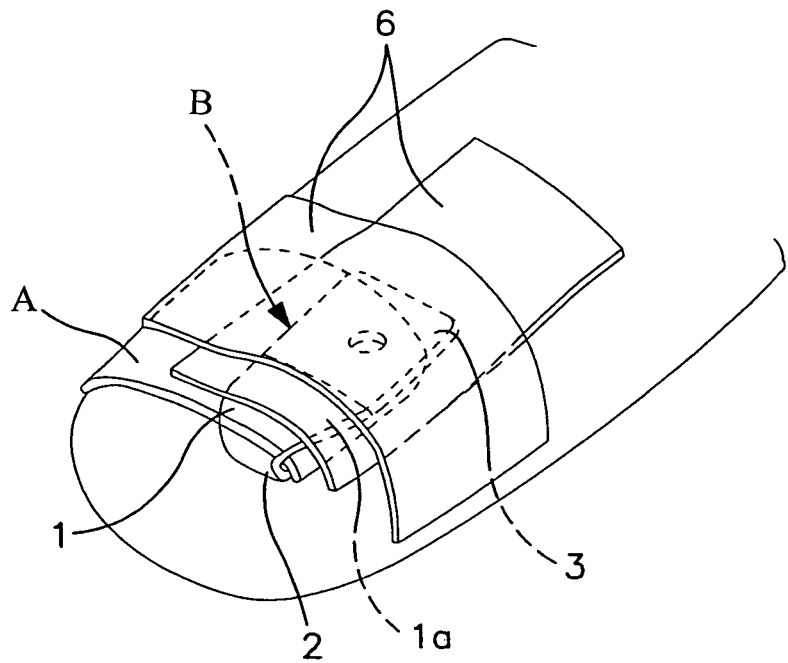
FIG. 5 is a perspective view of the ingrown nail correcting device in its fixed state.
Figure 6:
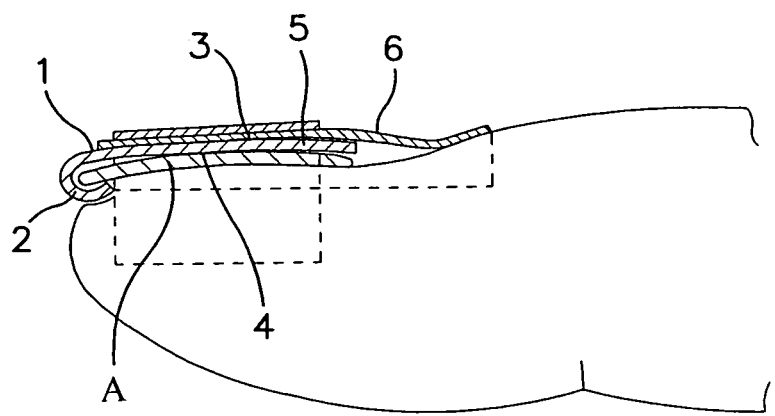
FIG. 6 is a longitudinal side elevation view of the ingrown nail correcting device in its fixed state.

Next, the lever member 3 pressed against the upper face of the nail A is fixed onto the dorsum of the toe or the thumb by the adhesive tape 6 as shown in FIGS. 5 and 6, by which the resilient corrective force to correct the ingrown nail by the leverage is maintained and the stable corrective force can be exerted over a long period of time. Further, the affected area protecting part 1a formed on a side of the main body 1 in a manner of forming a projecting arc shape covers the inflamed area caused by the ingrown nail, so that trouser bottoms can be prevented from coming into contact with the inflamed area or the other external force can be prevented from affecting the inflamed area.

The affected area protecting parts 1a, 1a are formed on both sides of the main body 1. Therefore, when the ingrown nail is found on the other side of the toe or the thumb, the ingrown nail correcting device B is arranged on this side having the ingrown nail so that the affected area protecting part 1a formed on the other side of the main body 1 can cover the affected area. However, the affected area protecting part 1a may be formed only on the side where the covering is needed.

Figure 7:
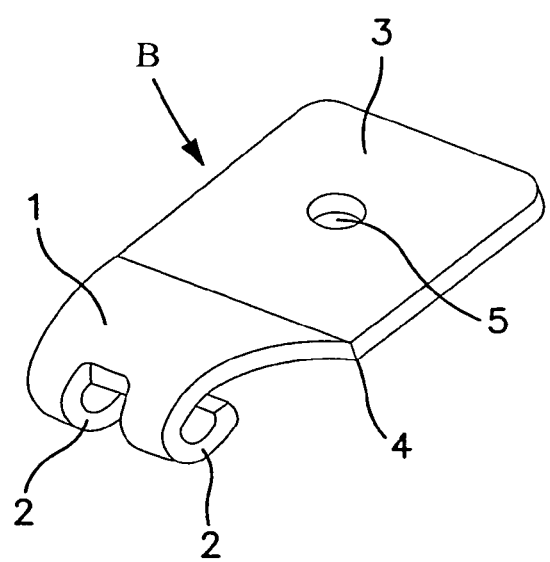
FIG. 7 is a perspective view showing another structure of the ingrown nail correcting device.

In the above-mentioned embodiment, the ingrown nail correcting device B is described in which the engaging member part 2 for correcting the ingrown nail is formed only at one position at the front end of the main body 1. However, as shown in FIG. 7, the part folded down and then backward from the front end of the main body 1 may be branched into two engaging member parts 2, 2. The structures of the other parts are the same as the above-mentioned embodiment, and details are not explained here while the same numbers and codes are put on the same parts. When the ingrown nail correcting device B is used, the adhesive tape 6 is used to maintain the state of pressing the lever member 3 against the nail surface by bonding the adhesive tape 6 on the upper surface of the lever member 3 and the toe surface or the finger surface, however, a first-aid adhesive tape or other fixing tapes may be used.

Figure 8:
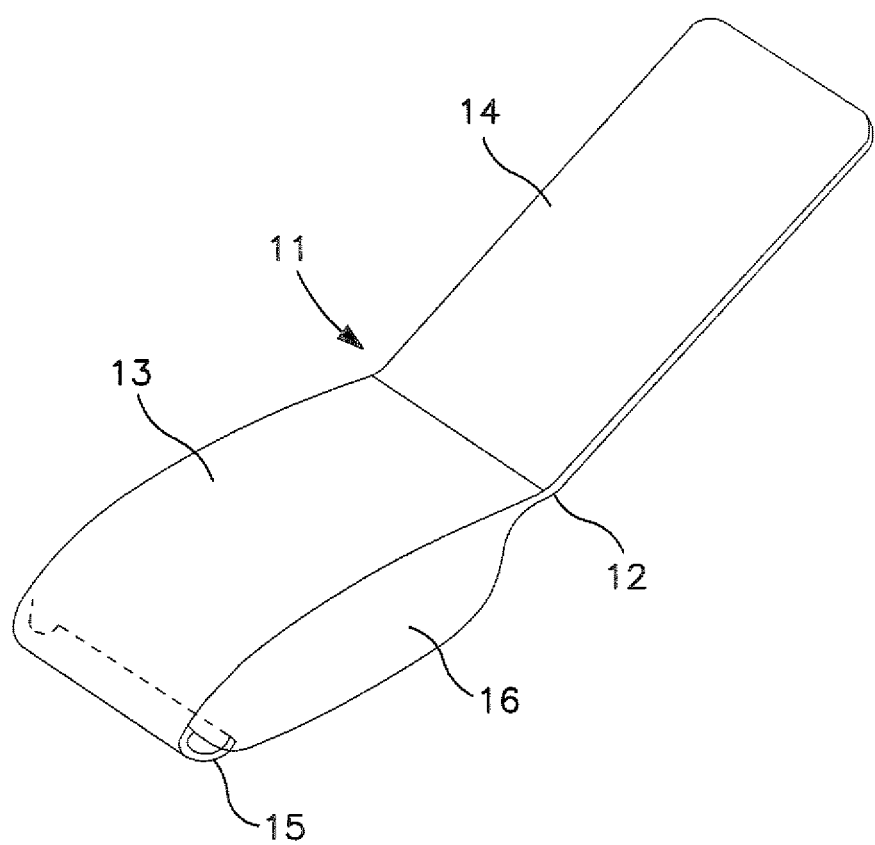
FIG. 8 is a perspective view of the ingrown nail correcting device main constituent according to the second embodiment.
Figure 9:
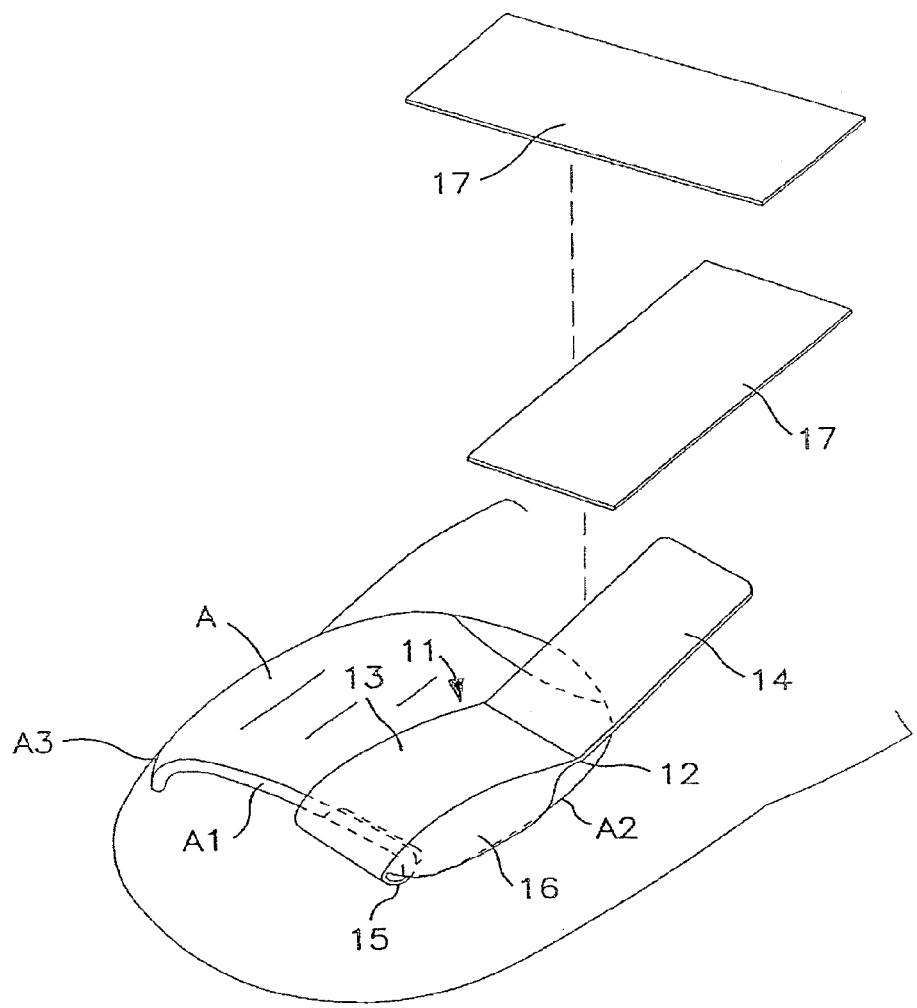
FIG. 9 is a perspective view of the ingrown nail corrective device in use.
Figure 10:
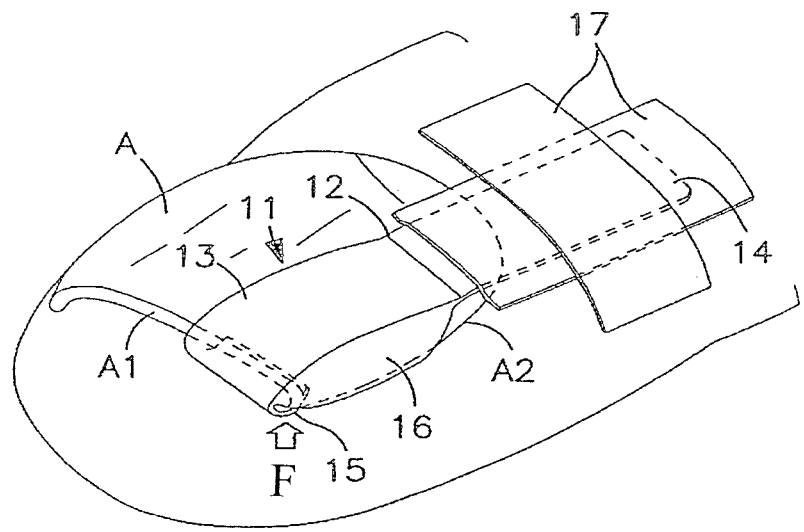
FIG. 10 is a perspective view of the corrective device in its state of use.

The second embodiment of this invention is explained hereinafter based on the drawings. FIG. 8 shows a perspective view of an ingrown nail correcting device main constituent, FIG. 9 shows a perspective view of the ingrown nail correcting device in use, and FIG. 10 shows a perspective view of the state of use. The ingrown nail correcting device main constituent 11 is formed of a thin rectangular metal plate or a hard and thin synthetic resin plate both having resilience. A longitudinal center of the thin plate is bent downward into a V-letter shape to form a fulcrum part 12. A front side of the fulcrum part 12 is formed to be an ingrown nail correcting element 13 and a rear side thereof is formed to be a lever member 14 which extends obliquely upward from a base end (a rear end) of the correcting element 13 in an extending direction of the correcting element 13. Further, a front end part of the correcting element 13 is folded down and then back to form a hook-shaped engaging member 15 to hook a front end A1 of the ingrown nail A. A laterally long protecting member 16 having a predetermined height is formed downward from a side end edge of the correcting element 13 in an integrating manner to cover a side end A2 of the ingrown nail A from its front end to its base end.

The ingrown nail correcting element 13 is formed to have the width of a quarter to a half of that of the ingrown nail A so that a side end of the engaging member 15 at the front end may be easily and surely engaged with a lower face of the front end of a side end A2 of the ingrown nail which curves downward, and the other side end of the engaging member 15 may be easily and surely engaged with the lower face of the front end A1 at the middle part, being the position of less than a half of the width of the nail from the side-end front of the ingrown nail A. The correcting element 13 is formed to have the length shorter than that of the ingrown nail A, so that the fulcrum part 12 provided at the base end may be positioned on the hard ingrown nail A when the engaging member 15 is engaged with the front end A1 of the ingrown nail A.

A larger angle of inclination of the lever member 14, namely, a larger angle of erection of the lever member 14 with respect to a longitudinal extension line of the correcting element 13, in the state that the engaging member 15 hooks the front end A1 of the ingrown nail A and that the correcting element 13 is placed on the ingrown nail A, makes the corrective force F for pulling up the engaging member 15 engaged with the front end of the ingrown nail A larger. However, when the angle is too large, the use becomes inconvenient and a pain may be caused. Therefore, the preferable range of angles is 30 to 40 degrees. The lengths of the correcting element 13 and the lever member 14 are substantially same, or the lever member 14 is formed to be a little longer.

The ingrown nail correcting device comprises the ingrown nail correcting device main constituent 11 formed as described above and an adhesive tape 17 of a proper length to fix the lever member 14 of the main constituent 11 in the state that the lever member 14 is pressed against the dorsum of the toe or the finger.

Figure 11:
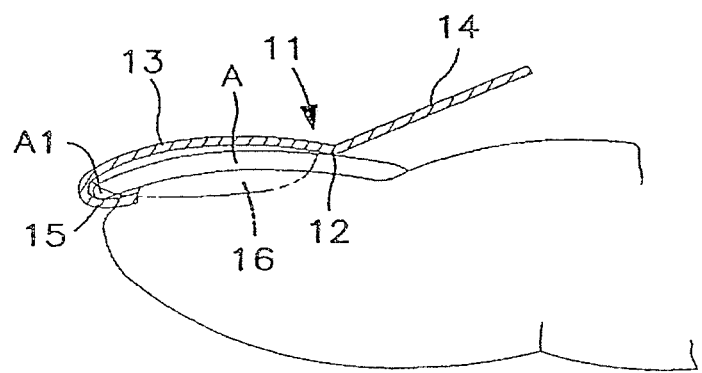
FIG. 11 is a longitudinal side elevation view of the state in which an engaging element is engaged with the front end of an ingrown nail.

Now, how the ingrown nail correcting device structured as above is used to correct the ingrown nail A is explained hereinafter. First, the correcting element 13 of the main constituent 11 is placed on a side of the ingrown nail A, and as shown in FIGS. 9, 11, a side end of the engaging member 15 at the front end of the correcting element 13 is set to hook and engage the lower face of the front end of the side end A2 of the ingrown nail A, and the other side end of the engaging member 15 is set to hook and engage the lower face of the front end A1 at the middle part, being the position of less than a half of the width of the nail from the side-end front of the ingrown nail A. The laterally long protecting member 16 projecting downward from a side end edge of the correcting element 13 is placed to cover the side end A2 of the ingrown nail A biting the toe or the finger over the whole length.

After that, the lever member 14 inclining obliquely upward in the rear direction from the base end of the correcting element 13 via the fulcrum part 12 is pressed down against the upper surface of the dorsum of the toe or the finger while allowing resilient deformation in a manner of nullifying the angle of inclination. Then the correcting element 13 moves in a direction of erecting the front end of the correcting element 13 by the leverage with the fulcrum part 12 serving as the fulcrum, and the pressing force of the lever member 14 as a force point. The action force for lifting the engaging member 15, formed from the front end part in a manner of being folded down and back, is generated and the action force works in the direction of correcting the front end of the ingrown nail A, biting the toe or the finger, which is engaged with the engaging member 15.

Figure 12:
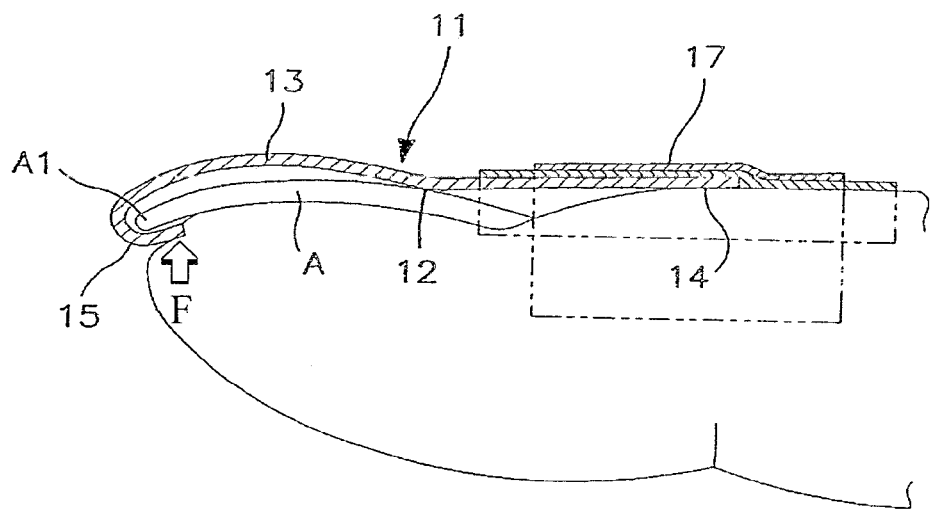
FIG. 12 is a longitudinal side elevation view showing the state of use.

Next, when the lever member 14 pressed against the upper surface of the dorsum of the tow or the finger is fixed to the dorsum by the adhesive tape 17 as shown in FIGS. 10, 12, the above-mentioned action force for lifting the front end of the ingrown nail A by the leverage, namely, the corrective force for correcting the ingrown nail A is maintained and a stable corrective force can be exerted over a long time. Further, the protecting member 16 projecting downward from the side end edge of the correcting element 13 covers the side end A2 of the ingrown nail A biting the toe or the finger over the substantially whole length thereof to externally protect it. In addition, a piece of absorbent cotton or a medical agent like an ointment may be placed between an inner face of the protecting member 16 and the part affected by the bite of the ingrown nail, as the need arises, whereby a maturation etc. of the affected part can be prevented or cured.

In the above-mentioned embodiment, the correcting device described above is for correcting the side end A2 of the ingrown nail A, while the structure of a correcting device for correcting the other side end A3 has the same structure as the above-mentioned correcting device except that the protecting member 16 is formed to bend downward from the other side end edge of the correcting element 13.

Figure 13:
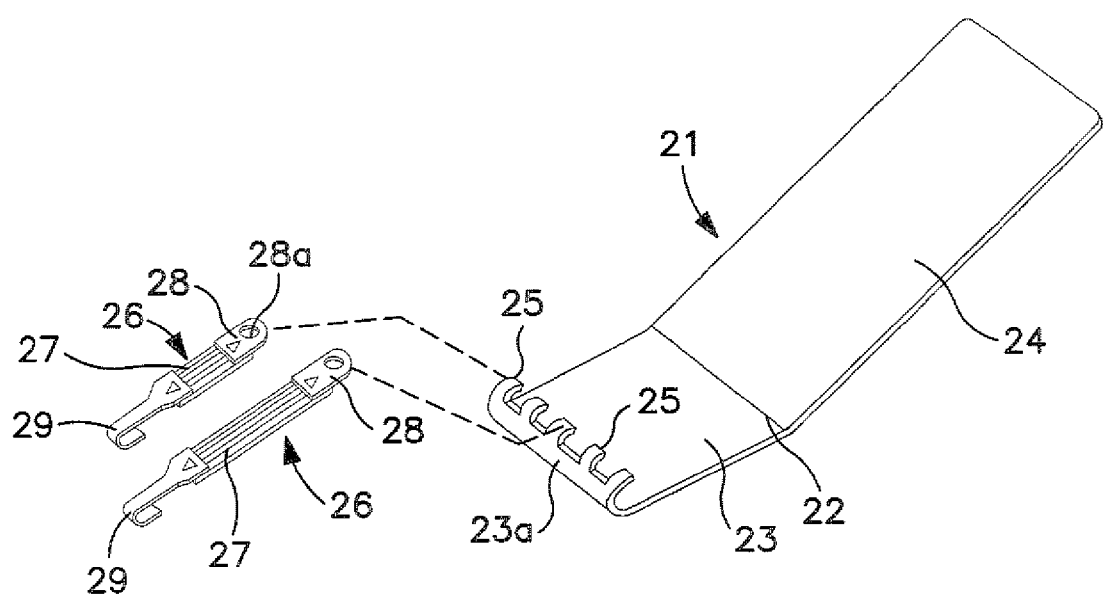
FIG. 13 is perspective views of the correcting device main constituent and the correcting member according to the third embodiment of this invention.
Figure 14:
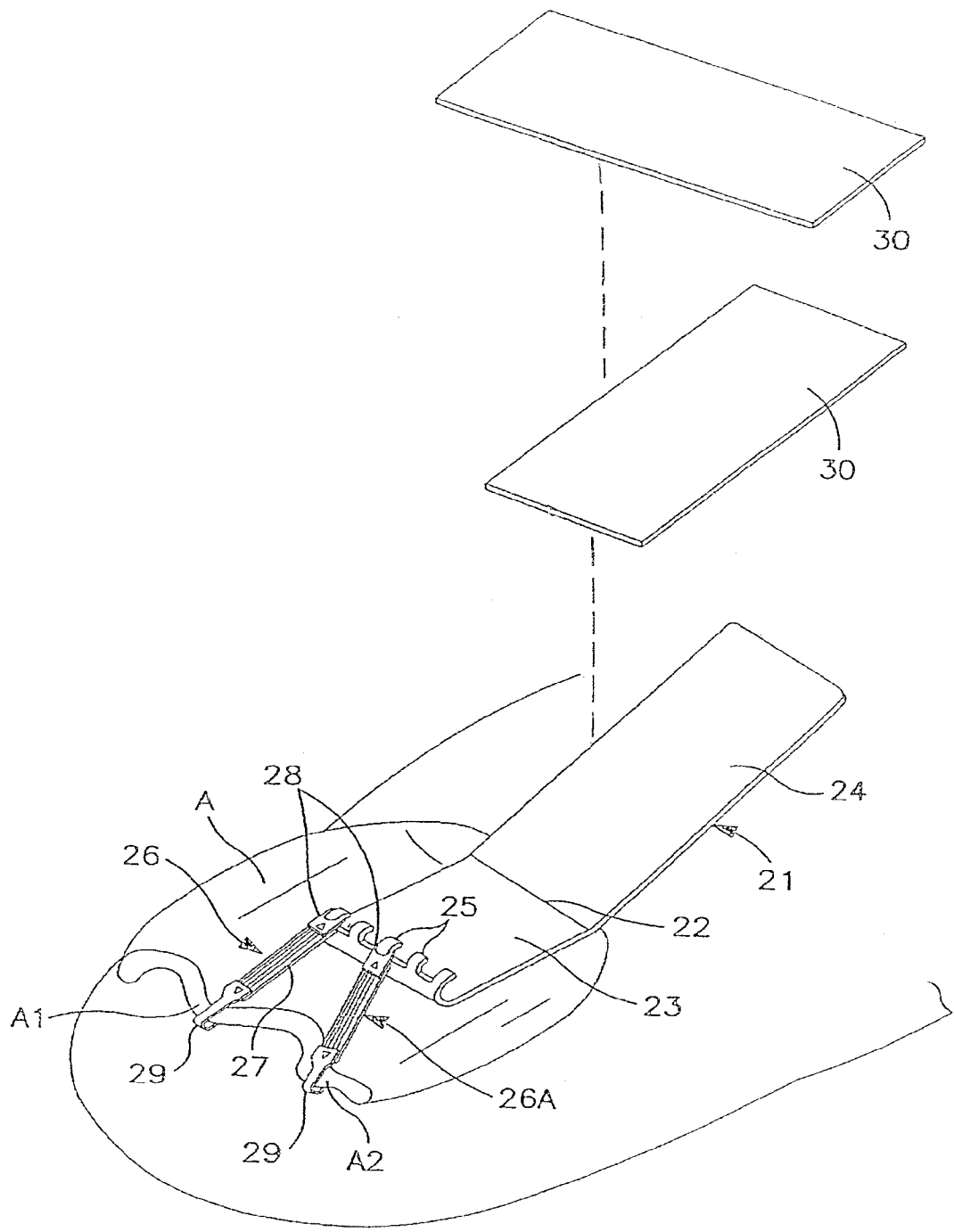
FIG. 14 is an exploded perspective view of the state in which the corrective device is fitted onto the dorsum of the nail.
Figure 15:
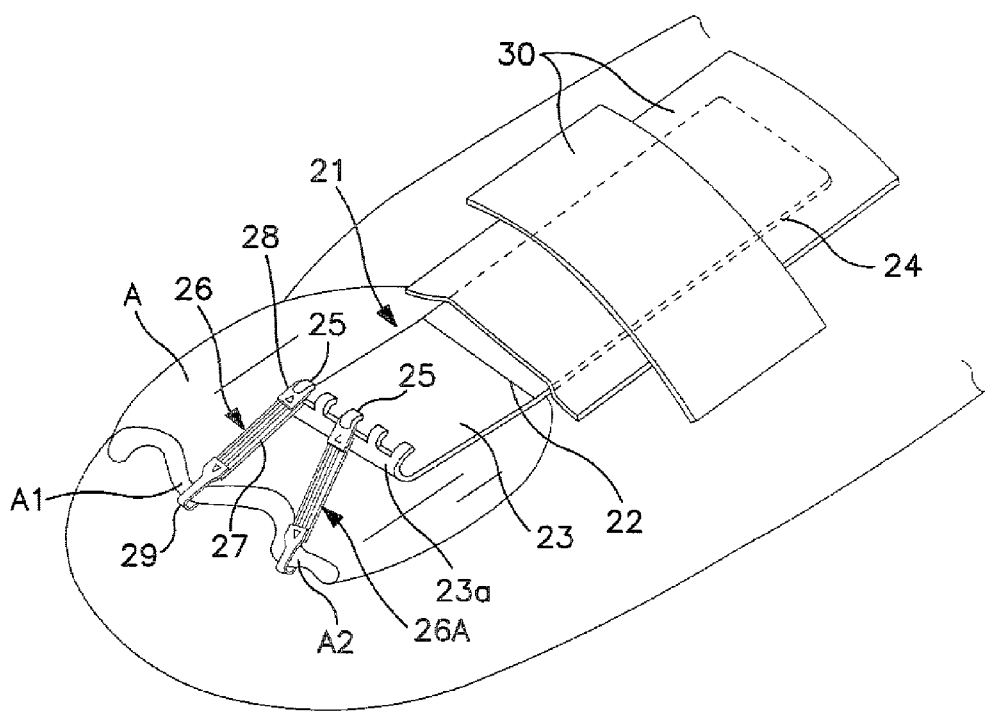
FIG. 15 is a perspective view showing a state of fitting.

The third embodiment of this invention is described hereinafter based on the drawings. In FIGS. 13 to 15, the correcting device for the ingrown nail A including a curved nail deformed to have a wavy front end comprises a correcting device main constituent 21 formed of a thin rectangular metal plate or a hard and thin synthetic resin plate, both having resilience, a correcting member 26 connected to a front end of the main constituent 21 in a manner that it can be engaged and disengaged, and a fixing member 30 like an adhesive tape for fixing the main constituent 21 onto the dorsum of the toe or the finger.

The main constituent 21 is formed to have a bent fulcrum part 22 by bending a longitudinal center part or the part closer to the front from the center part of the resilient rectangular thin plate downward into a V-letter shape. The front half from the bent fulcrum part 22 to the front end is formed to be an acting member 23 inclined obliquely upward from the bent fulcrum part 22 to the front end, and the rear half is formed to be a lever member 24 inclined obliquely upward from the bent fulcrum part 22 to the rear end. Further, a bent front end part 23a is formed by folding back the end of the acting member 23 upward so that it may be oriented to the lever member 24. A plurality of projecting hook-shaped engaging members 25 etc., are formed at the bent front end part 23a to be oriented to the lever member 24, namely backward, at small intervals in the width direction. The whole acting member 23 is formed to be like a rake by providing these engaging members 25 etc.

The lateral width of the correcting device main constituent 21 is a quarter to a half of that of the ingrown nail A, and the length of the acting member 23 of the main constituent 21 is shorter than that of the ingrown nail A so that the bent fulcrum part 22 provided at the base end may be positioned on an upper surface of the hard ingrown nail A upon correction of the ingrown nail. Further, when the angle of inclination of the lever member 24 with respect to the acting member 23, namely, the angle of erection with respect to a longitudinal extension line of the acting member 23 in its state of being placed on the ingrown nail A becomes larger, the corrective force acting on the ingrown nail A becomes larger. However, if the angle is too large, the use becomes inconvenient and a pain may be caused. Therefore, the preferable range of angle is 30 to 40 degrees.

The correcting member 26 to be connected to the front end of the main constituent 21 in a manner of being engageable and disengageable comprises an elastic strip 27 formed of a short rubber piece or rubber string of 1 cm long or shorter, an engaging element 28 arranged at the base end of the elastic strip 27 in an integrating manner and provided with an engaging hole 28a which can be engaged or disengaged with any one of the engaging members 25 etc. provided at the front end of the acting member 23 of the main constituent 21, and a hook-like correcting element 29 arranged in an integrating manner at the front end to hook the curved end part of the ingrown nail A.

Now, how the ingrown nail A is corrected by using the ingrown nail correcting device, which comprises the correcting device main constituent 21, the correcting member 26 and the fixing member 30 like the adhesive tape for fixing the main constituent 21 onto the dorsum of the toe or the finger, is explained hereinafter. Namely, as shown in FIG. 14, the acting member 23 of the main constituent 21 is placed on the ingrown nail A, and the hook-like correcting element 29 provided at the front end of the correcting member 26 is brought into the state of hooking the curved end part A1 of the ingrown nail A. In this state, the base end engaging element 28 of the correcting member 26 is engaged with any one of the plurality of the engaging members 25 etc. provided at the front end part of the acting member 23. When the ingrown nail A has two curved ends A1, A2 to be corrected, another hook-like correcting element 29 arranged at the front end of another correcting member 26A is brought to hook the second curved end A2, and the engaging element 28 of the correcting member 26A is engaged with any one of the engaging members 25 arranged at the front end part of the acting member 23.

As for the correcting member 26, a plurality of correcting members having different lengths and elasticity or having the same length and elasticity are made ready so that a proper correcting member 26 may be selected for use according to the shape and position of the curved end part of the ingrown nail A to be corrected, and the distance from the curved end part to the engaging element 28 of the main constituent 21, etc.

Next, the lever member 24 inclining obliquely upward in the rear direction from the base end of the acting member 23 of the main constituent 21 via the bent fulcrum part 22 is pressed down against the dorsum of the toe or the finger in the direction of nullifying the angle of inclination while allowing elastic deformation. Then the acting member 23 elastically acts in the direction of erecting the front end part by the leverage with the pressing force of the lever member 24 serving as a force point and the fulcrum part 22 serving as a fulcrum. The front end of the acting member 23 and the curved end part of the ingrown nail A are connected to each other by the correcting member 26. Therefore, when the angle formed by the acting member 23 and the lever member 24 becomes closer to 180 degrees as the lever member 24 is pressed down, the elastic force to move the front end up, namely, the tensile force for elastically pulling the base end of the correcting members 26, 26A engaged with the engaging members 25, 25 of the acting member 23 in the obliquely upper and rear direction becomes larger without lifting the front end of the acting member 23, virtually, with the fulcrum part 22 serving as the fulcrum. Because of the tensile force, the correcting elements 29 of the correcting members 26, 26A act as the corrective force in the direction of correcting the curved ends A1, A2 of the ingrown nail A, namely, in the direction of pulling up the curved ends A1, A2.

In this state, the lever member 24 pressed against the dorsum of the toe or the finger is fixed onto the dorsum by the fixing member 10 like the adhesive tape, as shown in FIG. 15, whereby the corrective force or the action force for lifting the front end of the ingrown nail A by the leverage, which is applied to the front end correcting elements 29 of the correcting members 26, 26A, is maintained, and the stable corrective force can be exerted for a long time.

Figure 16:
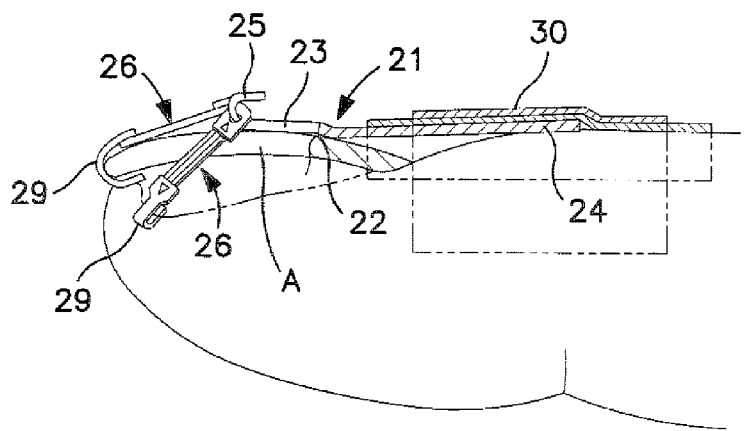
FIG. 16 is a longitudinal side elevation view of the state of correcting the ingrown nail and the front end curved parts.

In this embodiment, the front end correcting element 29 of the correcting member 26 hooks the curved end part A1 of the front end of the ingrown nail A, curving into a wave-shape in the lateral direction, to correct the curved end part A1, however, as shown in FIG. 16, the curved end part at the side end of the ingrown nail A can also be corrected by hooking the side end part with the correcting element 29 of the correcting member 26. When the ingrown nail A has a plurality of curved end parts to be corrected, the proper correcting members 26 suitable for the curved end parts are selected for use, respectively, which are engaged with the front end engaging members 25 of the acting member 23 of the constituent body 1.

ADVANTAGES OF THE INVENTION

According to a first aspect of the invention, since a hook-shaped engaging member part for hooking the ingrown nail is formed at the front end of the ingrown nail correcting device main body made of the hard resilient plate member, the engaging member part can be easily engaged with the front end of the ingrown nail protruding from the front end of the toe or the finger. In addition, a lever member inclining obliquely upward with respect to the main body is arranged at the base end of the main body in an integrating manner, and the bent part between the continuously-arranged main body and the lever member is formed to serve as a fulcrum part. Therefore, when a front end engaging member part of the main body is engaged with the front end of the ingrown nail and the fulcrum part is received by an upper surface of the nail, the lever member is brought into the state of inclining obliquely upward from the fulcrum part in the rear direction. Consequently, when the lever member is fixed to an upper surface of the nail by the fixing tape like the adhesive tape in a pressing manner, the lever member is resiliently pressed downward around the fulcrum part, the main body moves in the direction of erecting the front end side thereof by the leverage, and the corrective force for positively lifting the engaging member part engaged with the front end part of the ingrown nail is obtained, so that the ingrown nail can be effectively corrected.

Further, since the engaging member part is fixed by the fixing tape in the state that the engaging member part works in the direction of correcting the ingrown nail by the leverage, the ingrown nail corrective force can be exerted stably and effectively for a long period of time, so that the ingrown nail can be corrected. In addition, when the angle of inclination of the lever member, which is inclined obliquely upward with respect to the main body, is made to be 5 degree or less, the lever member immediately comes into contact with the nail surface upon pressing down the lever member, and the engaging member part engaged with the ingrown nail cannot exert a sufficient corrective force. When the angle of inclination is made to be 25 degree or above, the corrective force for resiliently pulling the ingrown nail up obtained by the engaging member part by fixing the ingrown nail correcting device in the state of pressing the lever member down to the upper surface of the nail by using the adhesive tape is exerted too much, which may cause pain, and a resilient restoring force of the lever member is increased causing difficulty in stably fixing the ingrown nail by the fixing tape. However, according to this invention, since the angle of inclination of the lever member inclining obliquely upward with respect to the main body is set to be 5 to 25 degrees, a stable ingrown nail corrective force by the leverage can be applied over a long time to correct the ingrown nail.

According to a second aspect of the invention, the main body is formed so that the lateral width between two side-end faces may be narrowed gradually from the longitudinal middle part to the front end. Further, at least one of the side-end faces of the main body, which is positioned on the affected side of the ingrown nail, is formed to be a curved side-end face having an outward projecting arc shape so that the side part may serve as an affected area protecting element. Therefore, the inflamed part caused by the bite etc. by the ingrown nail is covered by the affected area protecting element, so that the bottom of trousers or the like may be prevented from coming into contact with the affected area and from giving severe pain.

Furthermore, according to a third aspect of the invention, the main body is curved into a gently projecting arc shape from the fulcrum part toward the front end part. Therefore, the engaging member part can be engaged with the front end part of the ingrown nail smoothly and surely without being disturbed by the main body. In addition, when the fixing tape is wound around the affected toe or finger by the intermediary of the above-mentioned affected area protecting element, a clearance can be formed between the affected area protecting element and the affected area, so that the fixing tape may not be tightly stuck to the affected area and the affected area can be effectively protected.

According to a fourth aspect of the invention, the vent hole is formed in the lever member. Therefore, the air is allowed to pass out through the vent hole and the fixing tape like the adhesive tape having air permeability, so that the nail matrix, which is a breathing soft part of the root of the nail and is covered by the lever member, is prevented from becoming stuffy, and comfortable wearing is assured.

By forming the ingrown nail correcting device with the robustly resilient hard synthetic resin like a polycarbonate resin, the resilient resistance of the lever member, which is urged to bend downward around the fulcrum part, can be made comparatively large. Therefore, the sufficient corrective force required for correction of the ingrown nail can be stably applied via the leverage to the engaging member part engaged with the front end of the ingrown nail for a long period of time.

I claim:

1. An ingrown nail correcting device, said device comprising:
a main constituent having a front end, a lever member, and a plurality of correcting members, each correcting member having a base end and a front end,
the main constituent having an acting member of a predetermined length, said acting member being provided with a plurality of engaging members for engaging the base ends of said plurality of correcting members in an engageable and disengageable manner,
wherein each correcting member comprises a strip of material having an engaging element at its base end so that it may be engaged with the engaging member of the main constituent,
wherein each correcting member further includes a hook-shaped correcting element at its front end for hooking an ingrown nail, and
wherein each engaging member is hook-shaped and the engaging members are formed by dividing the front end of the acting member into a plurality of parts separated by small intervals, and the parts are folded upwardly into a rake-like shape.

2. An ingrown nail correcting device, said device comprising:
- a main constituent having a front end, a lever member, and a plurality of correcting members, each correcting member having a front end and a base end,
- the main constituent having an acting member of a predetermined length, said acting member being provided with a plurality of engaging members for engaging the base ends of said plurality of correcting members in an engageable and disengageable manner,
- wherein the lever member is connected at a joint to the acting member and extends obliquely upward with respect to the acting member,
- wherein said joint serves as a fulcrum,
- wherein the lever member is adapted to be secured against a toe or finger by a fixing member,
- wherein each correcting member comprises a strip of material having an engagement element at its base end so that it may be engaged with the engaging member of the main constituent, and
- wherein each correcting member further includes a hook-shaped correcting element at its front end for hooking an ingrown nail.

3. The ingrown nail correcting device of claim 2, wherein each engaging member is hook-shaped.

4. The ingrown nail correcting device of claim 3, wherein the engaging members are formed by dividing the front end of the acting member into a plurality of parts separated by small intervals, and the parts are folded upwardly into a rake-like shape.

5. The ingrown nail correcting device of claim 2, wherein the base end of each correcting member includes an engaging hole for engageable and disengageable attachment to an engaging member.

6. The ingrown nail correcting device of claim 5, wherein each correcting element is engaged with an engaging member.

7. The ingrown nail correcting device of claim 2, wherein each correcting member is constructed and arranged such that it may be engaged with the engaging member in an engageable and disengageable manner.

* * * * *